United States Patent
Thompson

[19]

[11] Patent Number: 5,846,249
[45] Date of Patent: Dec. 8, 1998

[54] VIDEO GYNECOLOGICAL EXAMINATION APPARATUS

[75] Inventor: Robert Lee Thompson, Dallas, Tex.

[73] Assignee: Pinotage, LLC, Fayetteville, Ark.

[21] Appl. No.: 730,089

[22] Filed: Oct. 15, 1996

[51] Int. Cl.$^6$ ..................................................... A61F 11/00
[52] U.S. Cl. .......................... 606/119; 600/220; 600/221; 600/109
[58] Field of Search ................................ 606/119, 13, 14; 600/220, 221, 224, 227, 223, 214, 184, 109, 102, 124, 125, 111, 112, 210, 211, 213, 219; 128/778, 775, 830–841

[56] References Cited

U.S. PATENT DOCUMENTS

| | | |
|---|---|---|
| 3,889,661 | 6/1975 | Fiore . |
| 4,046,140 | 9/1977 | Born . |
| 4,210,133 | 7/1980 | Castaneda ................................ 600/102 |
| 4,292,965 | 10/1981 | Nash et al. ............................... 128/833 |
| 4,619,248 | 10/1986 | Walsh ....................................... 600/223 |
| 4,638,792 | 1/1987 | Burgin . |
| 4,858,624 | 8/1989 | Shihata ..................................... 128/838 |
| 4,905,670 | 3/1990 | Adair ........................................ 600/104 |
| 4,979,498 | 12/1990 | Oneda et al. . |
| 5,143,054 | 9/1992 | Adair . |
| 5,251,613 | 10/1993 | Adair ........................................ 600/109 |
| 5,458,595 | 10/1995 | Tadir et al. .............................. 600/220 |
| 5,505,690 | 4/1996 | Patton et al. ............................ 600/214 |
| 5,509,893 | 4/1996 | Pracas . |
| 5,569,254 | 10/1996 | Carlson et al. . |

FOREIGN PATENT DOCUMENTS

| | | | |
|---|---|---|---|
| 1126036 | 11/1956 | France ................................... 600/220 |
| WO 93/20741 | 10/1993 | WIPO .................................... 600/220 |

*Primary Examiner*—Richard J. Apley
*Assistant Examiner*—Justine R. Yu
*Attorney, Agent, or Firm*—Wolf, Greenfield & Sacks, P.C.

[57] ABSTRACT

A charge-coupled device camera is removably mounted in a adaptor and the adaptor is removably mounted in the viewing aperture of a speculum. The camera is connected to a display device, such as a video monitor, by a cable. At least one high-intensity light is also mounted in the adaptor with the axis of the light parallel to that of the camera. The light is connected to an adjustable power source by a power supply cord. In one embodiment of the invention, a cervical positioner is provided to allow the physician to align the patient's cervix with the camera's axis for optimal viewing.

20 Claims, 3 Drawing Sheets

5,846,249

VIDEO GYNECOLOGICAL EXAMINATION APPARATUS

This application claims the benefit of prior filed copending U.S. Provisional Application Ser. No. 60/011,255 filed Feb. 7, 1996.

FIELD OF THE INVENTION

The present invention is related to an apparatus for conducting gynecological examinations using an electronic image receiving device such as a charge-coupled device.

SUMMARY OF THE INVENTION

A charge-coupled device camera is removably mounted in a adaptor and the adaptor is removably mounted in the viewing aperture of a speculum. The camera is connected to a display device, such as a video monitor, by a cable.

At least one high-intensity light is also mounted in the adaptor with the axis of the light parallel to that of the camera. The light is connected to an adjustable power source by a power supply cord.

In one embodiment of the invention, a cervical positioner is provided to allow the physician to align the patient's cervix with the camera's axis for optimal viewing.

BRIEF DESCRIPTION OF THE DRAWINGS

Two embodiments of the invention will be described, by way of example only, with reference to the accompanying drawings, in which.

DETAILED DESCRIPTION

Figure 1:
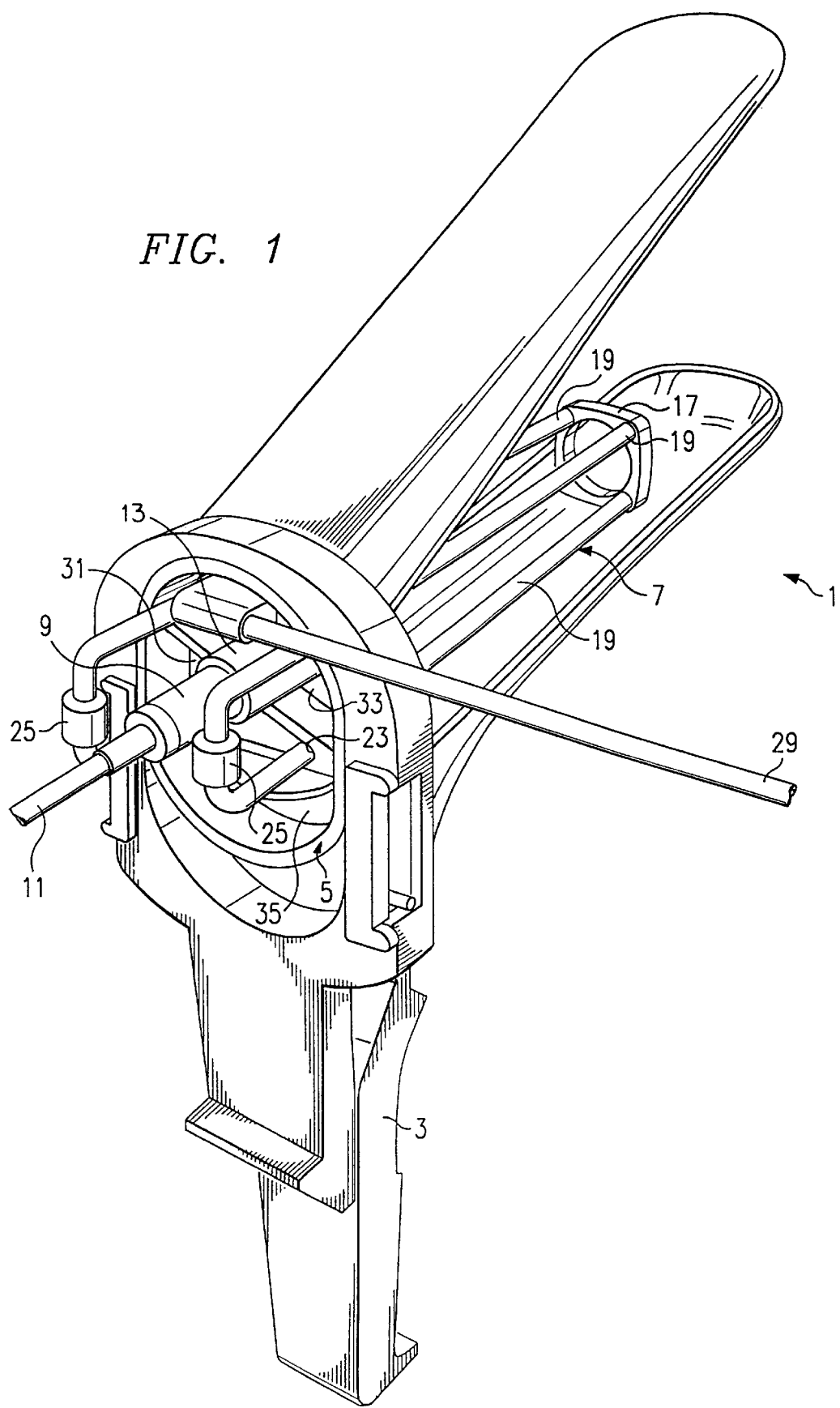
FIG. 1 is a perspective view of a video gynecological examination apparatus embodying the invention.
Figure 2:
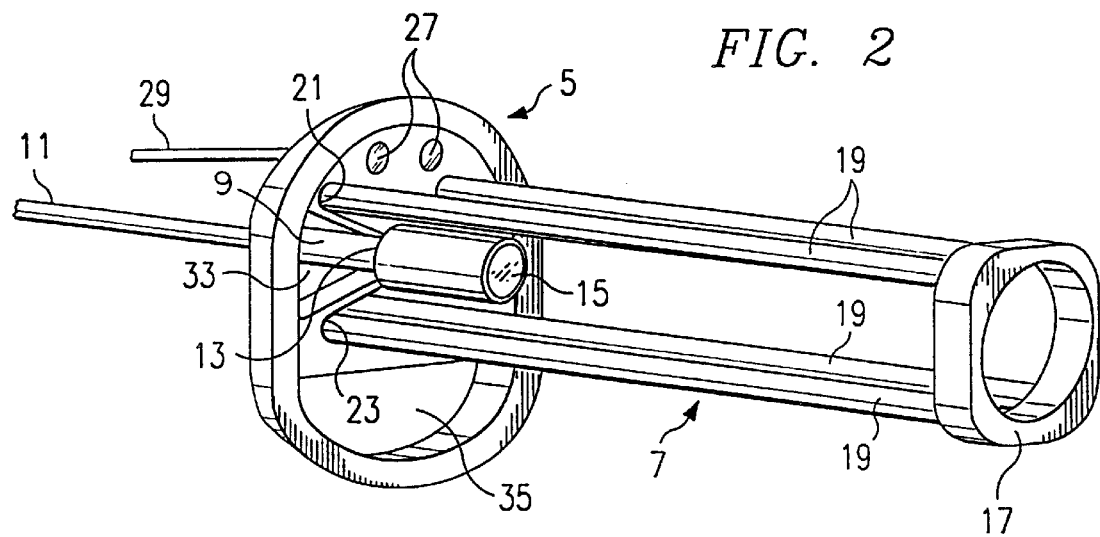
FIG. 2 is an opposing perspective view of the adaptor, camera, and cervical positioner of FIG. 1.

FIGS. 1 and 2 illustrate a video gynecological examination apparatus 1 in accordance with the present invention. The apparatus 1 comprises a conventional speculum 3, an adaptor 5, a movable cervical positioner 7, and a charge-coupled device ("CCD") camera 9. The camera 9 is connected to a video display (not shown) by a camera cable 11.

The adaptor 5 is constructed, for example, of a resilient plastic material, and is "snapped" into place in the speculum 3. In order to accommodate the specula of various manufacturers, a variety of suitably shaped and sized adaptors 5 are provided. The adaptor 5 is supplied in a sterilized condition and is intended to be disposed of after use. Alternately, if desired, the adaptor 5 could be constructed of a suitable material to allow it to be resterilized and reused.

The camera 9 is mounted in an integral camera mount 13. The inside diameter of the aperture in the camera mount 13 is just slightly greater than the outside diameter of the camera 9. This allows the camera 9 to be easily inserted and removed.

An optically clear window 15 is sealingly attached to the distal end of the camera mount 13. In use, the position of the portion of the camera 9 that is not within the camera mount 13 is such that it never comes into contact with the patient or any fluids from the patient. As a result, it is not necessary to sterilize the camera 9. This is a significant advantage, as it is not necessary to expose the camera 9 to the heat and/or liquid used in sterilization.

The cervical positioner 7 comprises a plastic cervical ring 17 and four plastic legs 19. To accommodate variations in cervical diameter, the cervical ring 17 is provided in several sizes. The cervical positioner 7 is supplied in a sterilized condition and is intended to be disposed of after use.

The distal end of the legs 19 are press fitted into corresponding orifices in the cervical ring 17. The proximal portions of the legs 19 pass through upper and lower slots 21, 23 in the adaptor 5. The legs 19 are resiliently biased outwardly, resulting in their being pressed against the outer edges of the slots 21, 23. The outer edges of the slots 21, 23 and the surface of the proximal portions of the legs 19 contain teeth (not shown) which cooperate to hold the legs 19 in position relative to the adaptor 5. The orientation of the teeth is such that the legs 19 may be easily pushed distally (from left to right in the drawings). To move the legs proximally (from right to left in the drawings), the legs 19 are moved inwardly to disengage the teeth, then pulled proximally.

The proximal ends of the legs 19 on each side of the adaptor are bent toward each other and connected by removable connecting members 25. In use, the legs 19 are moved as required to place the cervical ring 17 around the neck of the patient's cervix (not shown) and to position the patient's cervix in front of the camera 9. If necessary to properly position the cervix, the proximal ends of one or more legs 19 can be removed from the connecting members 25.

Two high-intensity lights 27 provide ample light for conducting an examination. The lights pressed into corresponding apertures in the adaptor 5. A power supply cord 29, connects the lights 27 to a controllable, low-voltage power supply (not shown).

Three apertures 31, 33, 35 are provided in the adaptor 5 to allow access to the patient's cervix when the examination apparatus 1 is in use.

The camera 5 is sensitive to both visible and infrared ("IR") light. To conduct an examination using visible light, the physician places an IR filter (not shown) on the distal end of the camera.

To conduct an examination of a patient's cervix (not shown), the examining physician (not shown) uses the speculum 3 to dilate the patient's vagina (not shown) in the conventional manner. The physician then adjusts the cervical positioner 7 to position the cervical ring 17 about the patient's cervix (not shown) and to position the cervix in front of the camera 9. The physician can then observe the patient's cervix on the display (not shown). If desired, a chemical agent can be applied to the patient's cervix using a conventional swab inserted through one of the apertures 31, 33, 35 in the adaptor 5.

The adaptor 5, cervical positioner 7, and connecting members 25 are provided in a sterilized condition and are intended to be disposed of after use.

Figure 3:
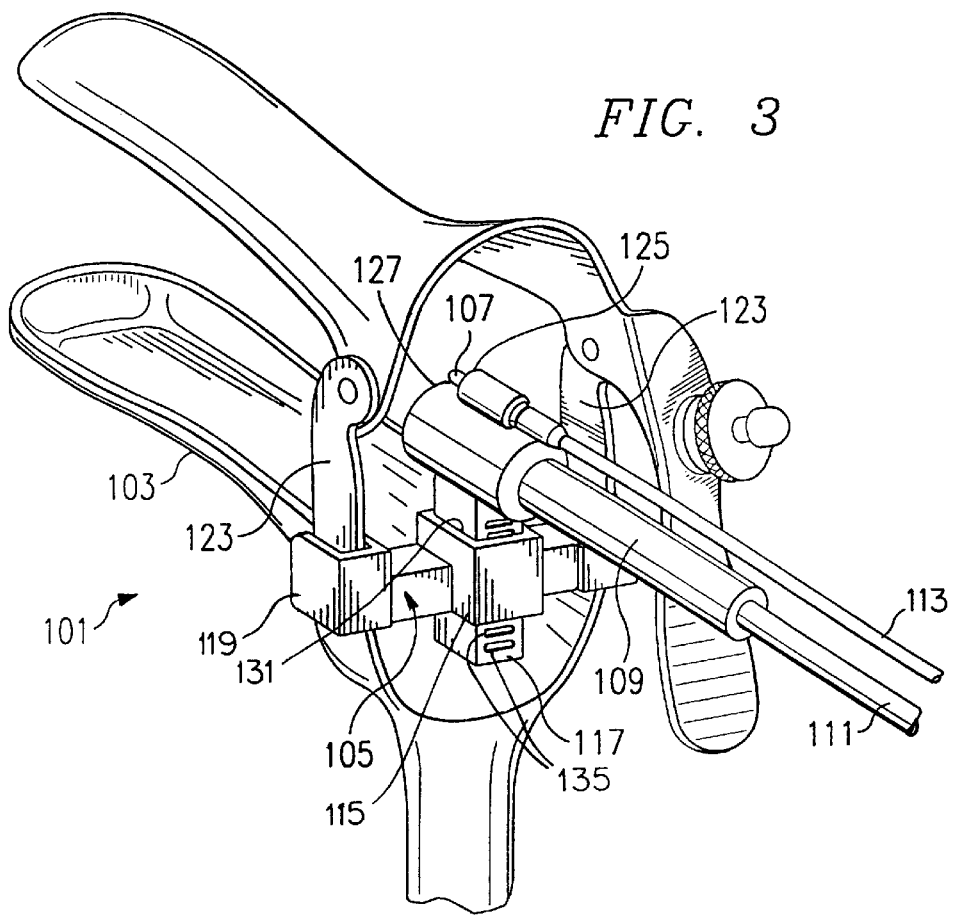
FIG. 3 is a perspective view of a second video gynecological examination apparatus embodying the invention.
Figure 4:
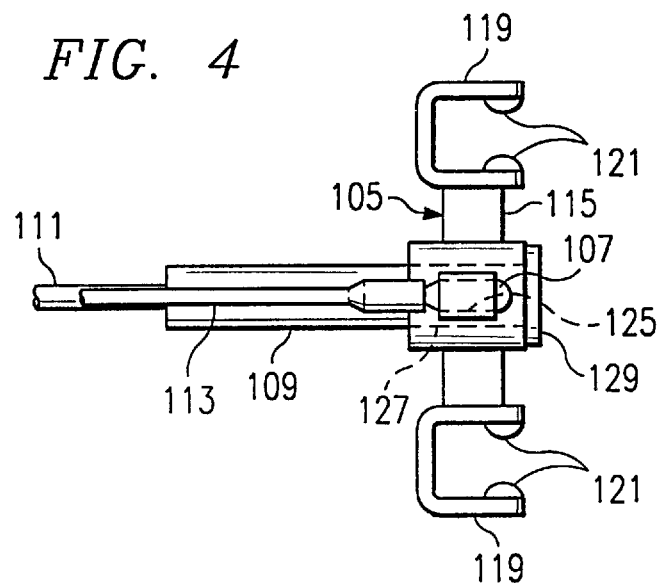
FIG. 4 is a top view of the adaptor and camera of FIG. 3.
Figure 5:
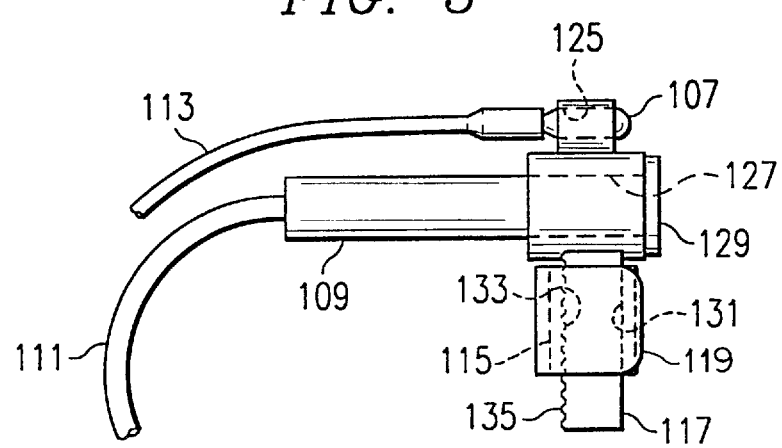
FIG. 5 is a side view of the adaptor and camera of FIG. 3.

FIGS. 3–5 illustrate a second video gynecological apparatus 101 in accordance with the present invention. The apparatus 101 comprises a conventional speculum 103 (only the upper portion of which is shown in FIG. 3), an adaptor 105, a high intensity light 107, and a CCD camera 109. In use, the camera 109 is connected to a video display (not shown) by a camera cable 111, and the light 107 is connected to an adjustable power supply (not shown) by a light cable 113.

As with the apparatus 1 described in connections with FIGS. 1 and 2, the adaptor 105 is constructed of a resilient material, such as plastic, and comprises a horizontal member 115 and a vertical member 117. An integral U-shaped clip 119 is disposed at either end of the horizontal member 115, and each clip 119 includes a pair of inwardly facing projections 121. In use, the adaptor 105 is removably attached to the arms 123 of the speculum 103 by means of the clips 119 on the horizontal member 115

The upper portion of the vertical member 117 includes a light aperture 125 and a camera aperture 127. An optically clear window 129 is sealingly attached at the distal end of the camera aperture 127. This provides the same advantage discussed in connection with the embodiment of the invention of FIG. 1 and 2.

The light aperture 125 provides a snug press fit for the high-intensity light 107, and the camera aperture 127 provides a similar fit for the camera 109. As a result, the light 107 and camera 109 can be easily installed in and removed from the adaptor 105.

As with the embodiment of the invention described in connection with FIGS. 1 and 2, the adaptor is constructed of a resilient plastic material, is provided in a sterilized condition, and is intended to be disposed of after use.

The lower portion of the vertical member 117 is slidably disposed in a complimentary aperture 131 in the horizontal member 115. The vertical member 117 is retained in position relative to the horizontal member 115 by the engagement of a series of inwardly-extending teeth 133 within the aperture 131 with a corresponding series of indentations 135 in the vertical member 117. As a result, the camera 109 and light 107 are vertically adjustable within the viewing aperture of the speculum 103. This allows the camera 109 and light 107 to be positioned for optimal viewing of the area of interest.

I claim:

1. A gynecological examination apparatus for use with a speculum to examine a gynecological site, the speculum including a first blade, a second blade, and a viewing aperture adjacent to a proximal end of the speculum, the apparatus comprising:

an adapter that is mountable in the viewing aperture, the adapter having a body; and an image receiving device, mounted to the adapter, having an optical viewing axis;

wherein the adapter includes means for altering a relative orientation between a position of the gynecological site and the image receiving device in at least one direction other than along the optical viewing axis, the means for altering the relative orientation between the position of the gynecological site and the image receiving device including a cervical ring to be placed about the gynecological site, and a plurality of legs that mount the cervical ring to the body of the adaptor and align the gynecological site with the image receiving device.

2. The apparatus of claim 1, wherein the adaptor is removably mountable in the viewing aperture.

3. The apparatus of claim 2, wherein the adapter further includes an aperture that receives the image receiving device, and the image receiving device is removably mounted in the aperture of the adaptor.

4. The apparatus of claim 3, wherein the adapter further includes a window that seals a distal end of the aperture of the adaptor to prevent contamination of the image receiving device.

5. A gynecological examination apparatus for use with a speculum to examine a cervix of a patient's body, the speculum having a viewing aperture, the apparatus comprising:

a camera having an optical viewing axis;

an adaptor that is mountable in the viewing aperture of the speculum and has a camera compartment to receive the camera, the camera compartment having a distal end and a window that seals the distal end and separates the camera from the patient's body, so that the camera need not be sterile when the apparatus is introduced into the patient's body; and a cervical positioner adapted to align the patient's cervix with the optical viewing axis of the camera, the cervical positioner having a first end, a second end, and at least one leg extending between the first end and the second end, the first end to be placed at the patient's cervix and the second end being mountable to the adapter.

6. The apparatus of claim 5, wherein the cervix positioner includes a ring that is adapted to be placed about the patient's cervix, and a plurality of legs that mount the ring to the adaptor.

7. The apparatus of claim 6, wherein the ring is removably mounted to the plurality of legs.

8. The apparatus of claim 6, wherein a first of the plurality of legs is positionable independently of a second of the plurality of legs.

9. The apparatus of claim 6, wherein each of the plurality of legs is positionable independently.

10. A gynecological examination apparatus for use with a speculum to examine a gynecological site of a patient, the apparatus comprising:

an adaptor that is mountable to the speculum, the adaptor having a camera compartment to receive a camera having an optical viewing axis; and a positioner, mountable to the speculum, to be placed about a cervix of the patient and position the gynecological site relative to the optical viewing axis of the camera.

11. The apparatus of claim 10, wherein the positioner is mounted to the adapter.

12. The apparatus of claim 10, wherein the speculum has a viewing aperture, and wherein the adaptor is removably mountable in the viewing aperture of the speculum.

13. The apparatus of claim 10, further comprising a camera that is removably mounted in the camera compartment.

14. The apparatus of claim 10, further comprising a light generating source that is mounted to the adaptor.

15. The apparatus of claim 14, wherein the adaptor includes an aperture that is constructed and arranged to receive an instrument for examining the gynecological site.

16. The apparatus of claim 15, wherein the positioner includes:

a ring that is placed about the cervix of the patient; and a plurality of adjustable legs that mount the ring to the adaptor.

17. The apparatus of claim 16, wherein the ring is removably mounted to the plurality of legs.

18. The apparatus of claim 16, wherein each of the plurality of legs is positionable independently.

19. The apparatus of claim 10, wherein the positioner includes:

a ring that is placed about the cervix of the patient; and a plurality of adjustable legs that mount the ring to the adaptor.

20. The apparatus of claim 19, wherein a first of the plurality of legs is positionable independently.

* * * * *